United States Patent
Al-Sofi et al.

(10) Patent No.: US 11,614,391 B1
(45) Date of Patent: Mar. 28, 2023

(54) EVALUATING GEL STABILITY BY INJECTION IN ALTERNATING FLOW DIRECTIONS

(71) Applicant: Saudi Arabian Oil Company, Dhahran (SA)

(72) Inventors: Abdulkareem M. Al-Sofi, Dhahran (SA); Jinxun Wang, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/511,644

(22) Filed: Oct. 27, 2021

(51) Int. Cl.
*G01N 11/00* (2006.01)
*G01N 33/24* (2006.01)
*G01N 15/08* (2006.01)
*E21B 33/138* (2006.01)
*E21B 49/02* (2006.01)

(52) U.S. Cl.
CPC .......... *G01N 11/00* (2013.01); *G01N 15/0826* (2013.01); *G01N 33/24* (2013.01); *E21B 33/138* (2013.01); *E21B 49/02* (2013.01)

(58) Field of Classification Search
CPC .... G01N 11/00; G01N 15/0826; G01N 33/24; E21B 33/138; E21B 49/02
See application file for complete search history.

(56) References Cited

U.S. PATENT DOCUMENTS

| | | |
|---|---|---|
| 3,785,437 A | 1/1974 | Clampitt et al. |
| 4,691,558 A | 9/1987 | Vinson et al. |
| 4,941,533 A | 7/1990 | Buller et al. |
| 5,042,296 A | 8/1991 | Burgess |
| 5,247,828 A | 9/1993 | Candau et al. |
| 5,261,267 A | 11/1993 | Kamath et al. |

(Continued)

FOREIGN PATENT DOCUMENTS

| | | |
|---|---|---|
| EP | 0188856 A1 | 7/1986 |
| GB | 2145420 A | 3/1985 |

(Continued)

OTHER PUBLICATIONS

AlSofi et al. "Portrayal and Demonstration of a Novel Procedure for In-Situ Estimation of Gelation Time" IOR 2019—20th European Symposium on Improved Oil Recovery Apr. 8-11, 2019, 8 pgs.

(Continued)

*Primary Examiner* — Ryan D Walsh
(74) *Attorney, Agent, or Firm* — Dinsmore & Shohl, LLP

(57) ABSTRACT

A method of evaluating gel stability of a gel for treating a subterranean formation includes placing a composite core plug into a core holder of a coreflood testing device where the composite core plug comprises first, second, and third core plugs, alternating injection of polymer solution into first and second injection areas, and monitoring a pressure drop across the composite core plug as a function of time. The method further includes identifying a gelation of a gelent solution in the third core plug, where the gelation is indicated by an increase in the pressure drop across the composite core plug, after the increase in the pressure drop indicative of the gelation point, continuing alternating injections of the polymer solution into the first and second injection areas, and identifying a reduction in the pressure drop across the composite core plug indicative of deterioration of the gel.

20 Claims, 3 Drawing Sheets

(56) References Cited

U.S. PATENT DOCUMENTS

| | | | |
|---|---|---|---|
| 5,992,223 | A | 11/1999 | Sabins et al. |
| 7,805,982 | B2 | 10/2010 | Hilab |
| 7,861,609 | B2 | 1/2011 | Haggerty et al. |
| 10,689,978 | B2 | 6/2020 | Al-Sofi et al. |
| 2006/0278390 | A1 | 12/2006 | Reddy et al. |
| 2018/0335374 | A1 | 11/2018 | Kanj et al. |
| 2019/0226970 | A1* | 7/2019 | Dusterhoft ......... G01N 15/0826 |
| 2019/0391065 | A1 | 12/2019 | Karazincir et al. |

FOREIGN PATENT DOCUMENTS

| | | |
|---|---|---|
| WO | 198600330 | 1/1986 |
| WO | 2011098770 A1 | 8/2011 |

OTHER PUBLICATIONS

Bertin et al. "Foam Flow in Heterogeneous Porous Media: Effect of Crossflow" SPE 39678, 1998, 13 pgs.

He et al. "Comparison of Gelation Behavior and Morphology of Resorcinol-Hexamethylenetetramine-HPAM Gel in Bulk and Porous Media" Transp Porous Med (2015) 109:377-392, 16 pgs.

Huang et al. "An Experimental Study of the In-Situ Gelation of Chromium(+3)/Polyacrylamide Polymer in Porous Media" SPE Reservoir Engineering, Nov. 1986, 10 pgs.

Hubbard et al. "Experimental and Theoretical Investigation of Time-Setting Polymer Gels in Porous Media" SPE Reservoir Engineering, Nov. 1988, 11 pgs.

Sengupta et al. "In-situ Gelation Studies of an Eco-friendly Cross-linked Polymer System for Water Shut-off at High Temperatures" Energy Sources, Part A, 36:1445-1467, 2014, 24 pgs.

Vasquez et al. "Laboratory Evaluation of High-Temperature Conformance Polymer Systems" SPE 80904, 2003, 11 pgs.

Vasquez et al. "Development and Evaluation of High-Temperature Conformance Polymer Systems" SPE 93156, 2005, 16 pgs.

Wang et al. "Developement and Evaluation of Gel-based Conformance Control for a High Salinity and High Temperature Carbonate" SPE-179796-MS, 2016, 14 pgs.

Zhuang et al. "A Novel EOR Polymer (II)—Investigation on In-Situ Gelation of SMRF System in Berea Core" Chinese Journal of Polymer Science, vol. 13 No. 1, 1995, 8 pgs.

International Search Report and Written Opinion dated Mar. 7, 2019, pertaining to Int'l Patent Application No. PCT/US2018/041359, 14 pgs.

* cited by examiner

EVALUATING GEL STABILITY BY INJECTION IN ALTERNATING FLOW DIRECTIONS

TECHNICAL FIELD

Embodiments of the present disclosure generally relate to production of hydrocarbons from subterranean hydrocarbon bearing formations, in particular to evaluating gel stability of gels for enhanced oil recovery from the subterranean hydrocarbon bearing formations.

BACKGROUND

Economic and efficient oil and gas production is dependent on understanding key properties of reservoir rock and fluid, such as porosity, permeability, compressibility, wettability, formation flow potential, fracture orientation, and fluid compatibility. Geoscientists have developed a variety of approaches, including log and core analysis techniques, to measure these properties. Core analysis is especially important in geologic formations with vertical and lateral heterogeneity. Core analysis can include evaluation of rock properties and anisotropy; organic matter content, maturity, and type; fluid content; fluid sensitivity; and geomechanical properties. This information can be used to calibrate log and seismic measurements and to help in well and completion design, well placement, and other aspects of reservoir production.

SUMMARY

Polymer gels have been widely applied as flow diverting or blocking agents in the treatment of injection and production wells for producing hydrocarbons from subterranean hydrocarbon bearing formations. These treatments are termed as conformance improvement, which is a common practice to improve oil recovery from a heterogeneous subterranean hydrocarbon-bearing formation. When a gelent solution comprising at least a water-soluble polymer and cross-linker is injected through injection wells, a solid-like gel system is formed in a portion of the subterranean hydrocarbon bearing formation after a certain duration of time. As a result, any subsequent injected water is diverted by the solid-like gel system to the un-swept or less-swept regions of the hydrocarbon bearing subterranean formation. In water shutoff applications, a gelent solution may be injected through production wells to block the pores of the formation to reduce or prevent the unwanted excess water and/or gas production from reaching the production well.

Both gelation time and gel long-term stability are among the important parameters for screening a gel formulation and characterizing the gel performance. Gelation time is the time when a gelent solution starts to form gel, which affects how far the gelent solution can be effectively placed deep into the formation. The gel long-term stability describes how long the gel can be effective in blocking or diverting the flow of displacing fluid before the gel degrades to the point where it is no longer effective as a barrier to flow through the formation.

Conventional methods for evaluating gelation time, gel long-term stability, or both include bottle tests and core flooding tests. Despite the availability of these conventional methods for gelation time, gel long-term stability, or both, these conventional methods are inaccurate and cannot use commercially available core plugs and coreholders. For example, conventional bottle tests, which are used to observe the gel syneresis as a measure of strength reducing of bulk gel, are often conducted at ambient pressure, and are more prone to evaporation during testing. Conventional core flooding tests require large core plugs and specialized core-holding setups, which are not commercially available. These core flooding tests are to measure a residual resistance factor, which is the ratio of water (injecting fluid) mobility before gel injection to the water mobility after gel treatment, by a coreflooding experiment. The residual resistance factor is usually measured only after a certain time period after gel formation in the core, and then re-measured at periodic time periods thereafter. As such, the gel remains in a static condition during formation of the gel and for the period between each measurement of the residual resistance factor. However, when injected into a subterranean hydrocarbon bearing formation, the gel is subjected to a dynamic flow environment in which the gel is constantly subjected to various flows of fluids through the subterranean hydrocarbon bearing formation. The forces caused by the fluid flow in the formation can impact the stability of the gel. Therefore, the conventional core tests that include long static periods in which the gel is not subjected to the forces caused by fluid flow against the gel can be inaccurate and can overestimate the gel stability of a gel system.

Thus, in order to determine in situ long-term gel stability of a gel or gel system, large core plugs with multipoint pressure measurements along the length have been used to simulate the dynamic flow conditions before and after gel is formed in porous media. Conventional coreholding setups cannot be used due to the large size of the core plugs required to accommodate the multipoint pressure measurements. Accordingly, ongoing needs exist for methods for accurately evaluating long-term gel stability of a gel or gel system in a core plug at in situ reservoir conditions utilizing commercially-available core plugs and coreholders.

Embodiments of the present disclosure are directed to methods of evaluating gel stability of a gel for treating subterranean hydrocarbon bearing formations. The methods of the present disclosure may include placing a composite core plug into a core holder of a coreflood testing device. The composite core plug may include a first core plug, a second core plug, and a third core plug disposed between the first core plug and the second core plug. The first core plug and second core plug may be saturated with a polymer solution, and the third core plug may be saturated with a gelent solution comprising at least a polymer and a cross-linker. The method may further include alternating injection of the polymer solution into a first injection area located on the first core plug and a second injection area located on the second core plug, and monitoring a pressure drop across the composite core plug as a function of time. The method may further include identifying a gelation of the gelent solution, where the gelation is indicated by an increase in the pressure drop across the composite core plug, after the increase in the pressure drop indicative of a gelation point, continuing alternating injections of the polymer solution into the first injection area and the second injection area, and identifying a reduction in the pressure drop across the composite core plug indicative of deterioration of the gel. The reduction in the pressure drop indicative of deterioration of the gel may include at least a 10% (percent) reduction in the pressure drop across the composite core plug over a period of less than or equal to 24 hours. The gel stability may be indicated by a time elapsed between the increase in the pressure drop indicative of gelation and the reduction in the pressure drop indicative of deterioration of the gel, and evaluated by the pressure response after the gel is formed. With alternating injection of the polymer solution into the composite core plug, the method of present disclosure may keep the gel in dynamic flow conditions before and after the gel is formed. Alternating injection may assure the gel in the third core plug does not outflow from the composite core plug. Thus, the method may accurately evaluate gel long-term stability in a core plug at in situ conditions by using a normal length of core plugs and conventional coreholders without multiple pressure taps in the middle of composite core plugs.

According to one or more aspects of the present disclosure, a method of evaluating gel stability of a gel for treating a subterranean formation may include placing a composite core plug into a core holder of a coreflood testing device. The composite core plug may comprise a first core plug, a second core plug, and a third core plug disposed between the first core plug and the second core plug. The first core plug and second core plug may be saturated with a polymer solution. The third core plug may be saturated with a gelent solution comprising at least a polymer and a crosslinker. The method may further include alternating injection of the polymer solution into a first injection area located on the first core plug and a second injection area located on the second core plug, monitoring a pressure drop across the composite core plug as a function of time, identifying a gelation of the gelent solution. The gelation may be indicated by an increase in the pressure drop across the composite core plug. The method may further include, after the increase in the pressure drop indicative of a gelation point, continuing alternating injections of the polymer solution into the first injection area and the second injection area and identifying a reduction in the pressure drop across the composite core plug indicative of deterioration of the gel. The reduction in the pressure drop indicative of deterioration of the gel may comprise at least a 10 percent (%) reduction in the pressure drop across the composite core plug over a period of less than or equal to 24 hours. The gel stability may be indicated by a time elapsed between the increase in the pressure drop indicative of gelation and the reduction in the pressure drop indicative of deterioration of the gel.

Additional features and advantages of the described embodiments will be set forth in the detailed description which follows, and in part will be readily apparent to those skilled in the art from that description or recognized by practicing the described embodiments, including the detailed description which follows as well as the drawings and the claims.

BRIEF DESCRIPTION OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
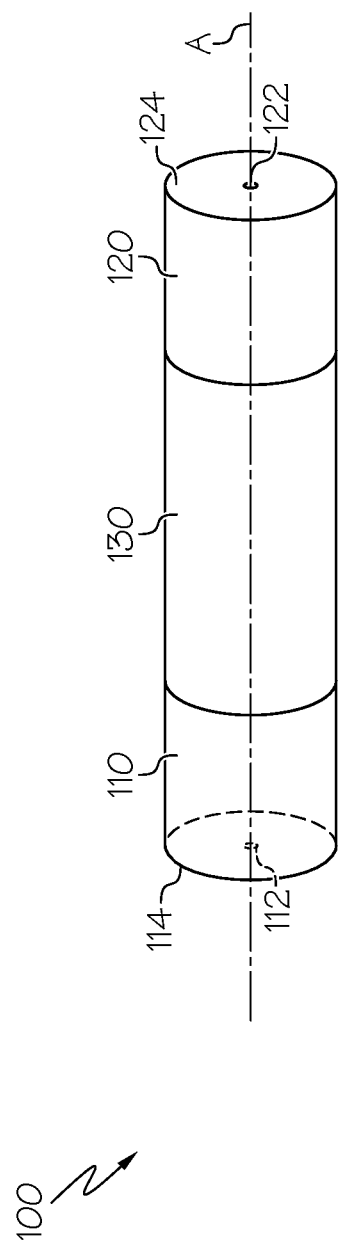
FIG. 1 schematically depicts a composite core plug comprising three core plugs abutted together to form the composite core plug, according to one or more embodiments shown and described in the present disclosure.

Embodiments of the present disclosure are directed to methods of evaluating gel stability of a gel for treating a subterranean formation, such as a subterranean hydrocarbon bearing subterranean formation. The methods of the present disclosure may include placing a composite core plug into a core holder of a coreflood testing device. The composite core plug may include a first core plug, a second core plug, and a third core plug disposed between the first core plug and the second core plug. The first core plug and second core plug may be saturated with a polymer solution. The third core plug may be saturated with a gelent solution comprising at least a polymer and a crosslinker. The method may further include alternating injection of the polymer solution into a first injection area located on the first core plug and a second injection area located on the second core plug, and monitoring a pressure drop across the composite core plug as a function of time. The method may further include identifying a gelation of the gelent solution. The gelation may be indicated by an increase in the pressure drop across the composite core plug. The method may further include, after the increase in the pressure drop indicative of a gelation point, continuing alternating injections of the polymer solution into the first injection area and the second injection area. The method may further include identifying a reduction in the pressure drop across the composite core plug indicative of deterioration of the gel. In embodiments, the reduction in the pressure drop indicative of deterioration of the gel may include at least a 10% reduction in the pressure drop across the composite core plug over a period of less than or equal to 24 hours. In embodiments, the deterioration of the gel may be indicated by the rate of change in the pressure drop as a function of time, such as a change in a slope of the pressure drop as a function of time. The start of deterioration of the gel may be marked by a starting point where a clear shift in pressure growth rates (decline in pressure growth rate) is observed while the complete or end of deterioration of the gel may be marked by another shift in pressure growth where differential roughly stabilize. The term "clear shift" may refer a shift which is visually apparent from the semilog plot (where pressure drop is plotted against time with time being in a log-scale). In embodiments, a clear shift may be as low as a two-fold decrease in the semi-log slope or for a normal plot and the absolute values a 10% decrease in the pressure decay rate in psi/hr (slope of a normal plot). The gel stability may be indicated by a time elapsed between the increase in the pressure drop indicative of gelation and the reduction in the pressure drop, change in the slope of pressure drop as a function of time, or both indicative of deterioration of the gel. The alternating injections of the polymer solution into the composite core plug may enable keeping the gel in a dynamic flow condition before and after the gel is formed without outflow. Thus, the method may accurately evaluate gel long-term stability in a core plug at in situ conditions by using a normal length of core plugs and conventional coreholders without multiple pressure taps in the middle of the composite core plugs.

The methods of present disclosure may also provide an indication of the gelation time of the gel. The term "gelation time" may refer a time when a gel solution starts to form gel. The gelation time of the gelent solution in the third core plug may be determined by monitoring the pressure drop, or pressure profile change, across the composite core plug during the alternating injections of polymer solution. The gelation time may be determined through monitoring the pressure response while the gelent solution resides in the third core plug. In-situ gelation times can be determined using normal length core or core composite, with conventional coreholders, and without the need for multiple pressure taps. Once the gelation time is reached, conventional methods of evaluating gelation time may be ceased and the core plugs may be removed from the coreholders. In the methods of the present disclosure, the alternating injections may be continued well past gelation of the gelent solution to the initiation of syneresis to evaluate gel stability. Continuing the alternating injections of polymer solutions past the gelation time may enable evaluating not only gelation time but also the long-term stability of the gel. Thus, the methods of present disclosure may enable evaluation of gel stability, after the gelation time is reached, by using standard sized core plugs and coreholders with improved accuracy. Other features and benefits of the present disclosure may become apparent to persons of ordinary skill of the art from practicing the subject matter of the present disclosure.

As used throughout this disclosure, the term "composite core plug" may refer to a core plug having one or more cylindrical sections arranged axial end to axial end.

As used throughout this disclosure, the term "core plug" may refer to a plug, or sample, taken from a whole core from a formation for analysis. Core plugs are conventionally 1 to 1.5 inches (in.) (2.5 to 3.8 centimeters (cm); 1 in.=2.54 cm) in diameter and 1 to 2 in (2.5 to 5 cm) long. Core plugs are conventionally cut perpendicular to the axis of the core or parallel to the axis, which form horizontal and vertical plugs, respectively, when cut from a vertical wellbore. Conventional core plug analysis is conducted in a coreholder.

As used throughout this disclosure, the term "coreflooding" may refer to a test in which a fluid or combination of fluids is injected into a core plug. Objectives of coreflooding may include but are not limited to measurement of permeability, relative permeability, saturation change, formation damage caused by the fluid injection, or interactions between the fluid and the rock, such as the gelation time and gel stability of the fluid. The core material may come from an oil reservoir, but some tests may use outcrop rock. The fluid in place at the start of the test is typically either a simulated formation brine, oil, or a combination of brine and oil. Injected fluids may include crude oil, simulated reservoir brine, refined fluids, drilling mud filtrate, acids, foams, gelent solutions, or other chemicals used in the oil field. Pressures and flow rates at both ends of the core may be measured.

As used throughout this disclosure, the term "coreholder" may refer to a vessel designed to withstand elevated temperatures and pressures, such as up to 20,000 pounds per square inch (psi) (137,895 kilopascals (kPa); 1 psi=6.89476 kPa) and 300° C., and to test core plugs at these elevated temperatures and pressures.

As used throughout this disclosure, the term "coreflooding coreholder" may refer to a coreholder vessel equipped to conduct coreflooding experiments and measurements, including coreflooding gel stability testing.

As used throughout this disclosure, the term "formation" may refer to a body of rock that is sufficiently distinctive and continuous from the surrounding rock bodies that the body of rock can be mapped as a distinct entity. A formation is, therefore, sufficiently homogenous to form a single identifiable unit containing similar rheological properties throughout the formation, including, but not limited to, porosity and permeability. A formation is the fundamental unit of lithostratigraphy.

As used throughout this disclosure, the term "reservoir" may refer to a subsurface formation having sufficient porosity and permeability to store and transmit fluids. As used throughout this disclosure, the term "subterranean hydrocarbon-bearing formation" may refer to a subterranean geologic region containing hydrocarbons, such as crude oil, hydrocarbon gases, or both, which may be extracted from the subterranean geologic region. The terms "subterranean formation" or just "formation" may refer to a subterranean geologic region that contains hydrocarbons or a subterranean geologic region proximate to a hydrocarbon-bearing formation, such as a subterranean geologic region to be treated for purposes of enhanced oil recovery or reduction of water production.

As used throughout this disclosure, the term "pore volume" may refer to the ratio of void space to total bulk volume for a material and is indicative of the volume of pores within the a core plug.

As used throughout this disclosure, the term "saturated" may refer to the almost complete filling (such as 0.6 pore volume (PV), 0.8 PV, 0.9 PV, 0.95 PV, or 0.99 PV or above) of the core sample pore volume with a given fluid.

As used throughout this disclosure, the term "viscous fingering" may refer to a phenomena whereby the interface of two fluids, in which one fluid has a lesser viscosity than the other, such as a difference of more than 5 centiPoise (cP), 10 cP, 20 cP, or 50 cP, and bypasses sections of the porous media as it moves along, creating an uneven, or fingered, profile. Fingering is a relatively common condition when injecting solutions with a viscosity of less than 10 cP into porous media.

As used throughout this disclosure, the term "whole core" may refer to a complete section of a conventionally-drilled core. The section may be up to approximately 2 feet ((60 cm); 1 foot=30.48 cm) in length, with conventional core diameters lying between 1.75 and 5.25 in. (4.4 and 13.3 cm).

Figure 2:
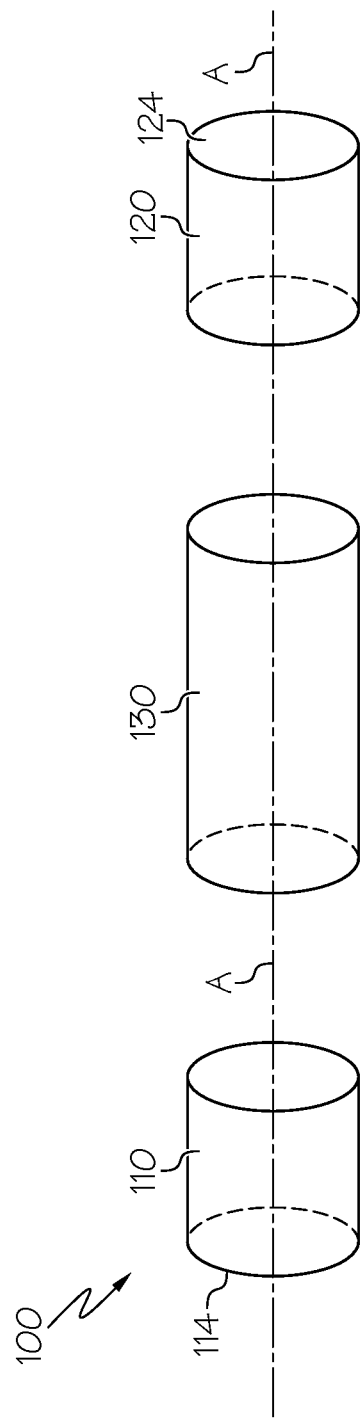
FIG. 2 schematically depicts an exploded view of the composite core plug of FIG. 1, according to one or more embodiments shown and described in the present disclosure.

As used throughout this disclosure, the term "axial" may refer to a direction parallel to the center axis A of the composite core plug 100 of FIGS. 1 and 2. As used throughout this disclosure, the term "axial surface" may refer to a surface of a core plug that is perpendicular to the center axis A of the composite core plug 100 of FIGS. 1 and 2.

The present disclosure is directed to methods for evaluating gel stability of a gel for treating subterranean formations. The methods may include placing a composite core plug into a coreholder of a coreflood testing device. The coreholder may be a commercially-available coreholder. The composite core plug may include a first core plug, a second core plug, and a third core plug disposed between the first core plug and the second core plug. The method may further include alternating injections of the polymer solution into a first injection area located on the first core plug and a second injection area located on the second core plug. The injection area may include a point on, a part of, or the entirety of the exposed end, face, or surface of the first core plug or the second core plug. The polymer solution may be injected in an injection point or may be injected along the entire exposed face of the first core plug or the second core plug.

The method may further include monitoring a pressure drop across the composite core plug as a function of time. The pressure drop may be monitored during the alternating injection of polymer solution to determine the gel long-term stability of the gelent solution in the third core plug. The term "gel stability" may refer to the ability of a gel to block the pores of a formation and maintain a barrier to fluid flow through the formation for an extended period of time. The gel stability of a gel may be characterized by a time between gelation of the gelent solution and a time at which disintegration of the gel begins, a strength of disintegration, a speed of disintegration, or combinations thereof. The gel stability may be indicated by a time elapsed between the increase in the pressure drop indicative of gelation of the gelent solution to form the gel and the reduction in the pressure drop indicative of the start of deterioration of the gel. The strength of disintegration may be determined by a percentage of permeability restoration or the value of a residual resistance factor (RRF). The permeability may be significantly decreased after the formation of gel, and the permeability will gradually restore (increase) during the process of gel disintegration. The RRF may be also an indicator of gel blockage efficiency. The RRF may be high when a strong gel blocks most of the flow path through the composite core plug and may decrease after the start of gel disintegration. RRF is the ratio of water (injecting fluid) mobility before gel injection to the water mobility after gel treatment. The RFF is a measure of the water permeability reduction after the application of gel treatment. If the water is injected at a same flow rate before and after gel injection, then the residual resistance factor can be calculated as follows, $$RRF = \frac{\lambda_w}{\lambda'_w} = \frac{k_w}{k'_w} = \frac{\Delta P'_w}{\Delta P_w}$$

where $\lambda_w$, $k_w$, and $\Delta P_w$ are water mobility, water permeability and pressure drop before gel injection, respectively. $\lambda'_w$, $k'_w$ and $\Delta P'_w$ are water mobility, water permeability and pressure drop after gel injection, respectively.

Figure 3:
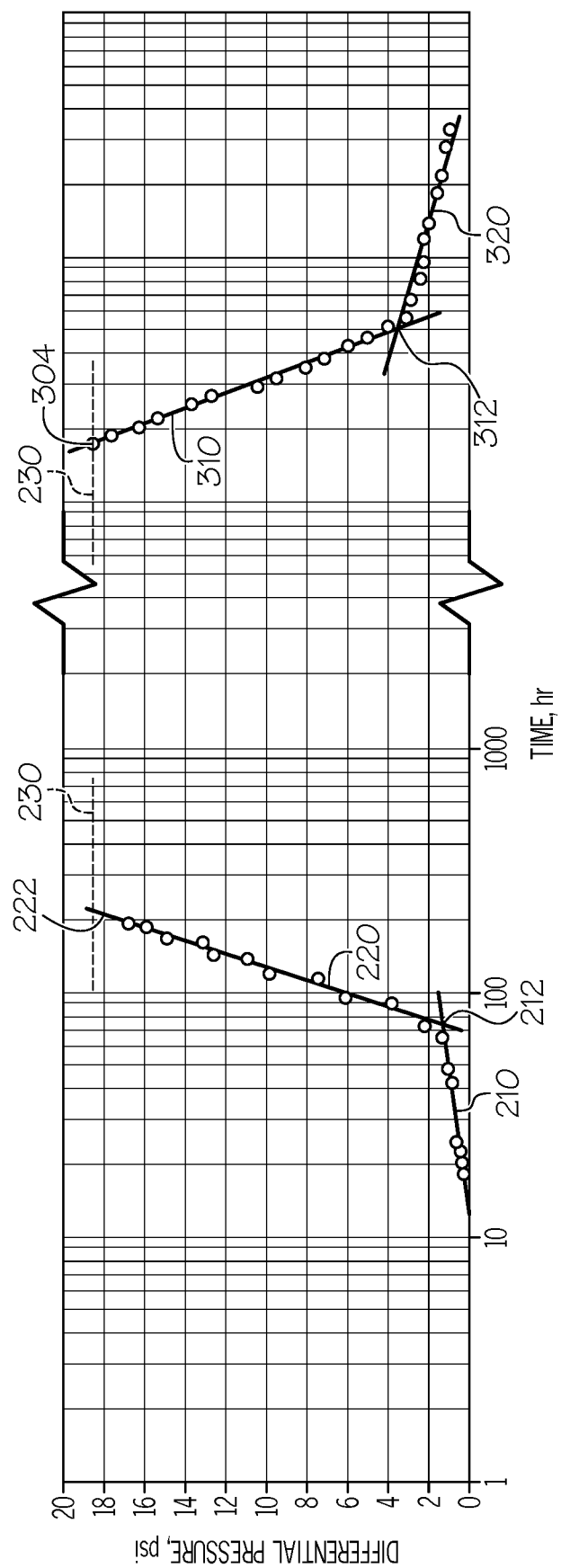
FIG. 3 graphically depicts a differential pressure (y-axis) as a function of the logarithm of time (x-axis) during gelation time and gel stability testing, according to one or more embodiments shown and described in the present disclosure.

The speed of disintegration may be determined by the disintegration time, which is the duration of time that elapses between the start of disintegration of the gel and the point where the pressure drop as a function of time indicates that obstructions to flow are insignificant. Lines 310 and 320 in FIG. 3 show the pressure drop trend as a function of the logarithm of time during the disintegration process. As shown in FIG. 3, the pressure drop decreases faster at first (line 310). After some time indicated by point 312 in FIG. 3, the decrease in the pressure drop tends to be slower (line 320). If the slope of line 310 is less steep, or the duration time of this first stage of pressure dropping is longer, then it may indicate that the disintegration strength is stronger. The disintegration process does not end at the crossover point of 312 in FIG. 3. The insignificant reduction in the pressure drop may indicate the complete disintegration of the gel. The term "insignificant reduction in the pressure drop" may refer to a pressure decay rate that is lower than 1 psi/hr or as defined earlier a pressure decay rate that is semi-logarithmically two-folds lower than initially observed pressure decay rates (i.e. at least 10% lower than initial rates in psi/hr).

Referring now to FIG. 1, a composite core plug 100 according to the present disclosure is schematically depicted. The composite core plug 100 may be placed into the coreholder of a coreflood testing device. The composite core plug 100 may include a first core plug 110, a second core plug 120, and a third core plug 130 disposed between the first core plug 110 and the second core plug 120. Each core plug may be cylindrical in shape. The first core plug 110 and the second core plug 120 may each be in contact with each respective end of the third core plug 130. In other words, the first core plug 110 may be positioned so that a flat axial surface of the first core plug 110 may contact and abut against a first flat axial surface of the third core plug 130. Likewise, the second core plug 120 may be positioned so that a flat axial surface of the second core plug 120 may contact and abut against a second flat axial surface of the third core plug 130. The flat axial surfaces of the first core plug 110 and the third core plug 130 may be abut against each other on one end of the third core plug 130, and the flat axial surfaces of the second core plug 120 and the third core plug 130 may abut against each other on the opposite end of the third core plug 130. In embodiments, the diameter, porosity, and permeability of the first core plug 110 and the second core plug 120 may be within 0.1% (percent), 0.5%, 1%, 2%, or 5% of a diameter, porosity, and permeability of the third core plug 130. The first core plug 110 and the second core plug 120 may be cut from the same whole core and, thus, may have the same diameter, porosity, and permeability.

The first core plug 110 and the second core plug 120 may be saturated with polymer solution. Saturating the first and second core plugs with polymer solution, instead of an aqueous solution, may minimize viscous fingering and dispersion of the injected fluid into the gelent solution during subsequent injections, due to the similar viscosities of the polymer solution and the gelent solution.

The polymer solution may include a polymer and a diluent. The polymer solution may include polymer without a crosslinker. The polymer may include at least one of polyacrylamide, acrylamide copolymers, biopolymers, polysaccharides, and xanthan gum. Biopolymers may include polymeric biomolecules, or polymers produced by living organisms. The three main classes of biopolymers may be polynucleotides, polypeptides, and polysaccharides.

Polysaccharides may include linear bonded polymeric carbohydrate structures. Xanthan gum may include a polysaccharide that may be used as a thickening agent and stabilizer. Other possible polysaccharides may include, but are not limited to, schizophyllan and scleroglucan. In embodiments, the polymer of the polymer solution may have a weight averaged molecular weight of from 10 million Daltons to 30 million Daltons, from 15 million Daltons to 30 million Daltons, from 10 million Daltons to 25 million Daltons, from 15 million Daltons to 25 million Daltons, from 10 million Daltons to 20 million Daltons, or from 15 million Daltons to 20 million Daltons. In embodiments, the polymer of the polymer solution may be at least partially hydrolized. In embodiments, the polymer of the polymer solution may have a degree of hydrolysis of from 20% to 40%, from 20% to 35%, from 20% to 30%, from 25% to 40%, from 25% to 35%, from 25% to 30%, or 30%. The diluent may be water or any other appropriate diluent.

The polymer solution may have a viscosity of greater than 50 cP, greater than 20 cP, greater than 15 cP, greater than 10 cP, greater than 8 cP, greater than 5 cP, or greater than 2 cP to saturate the first core plug 110 and the second core plug 120 to minimize the dilution of the polymer concentration in the gelent solution due to mixing. In embodiments, the polymer solution may have a viscosity within 1%, 3%, 5%, 10%, 20%, or 50% of a viscosity of the gelent solution before gelation. In embodiments, the polymer solution may have a viscosity within 5% of a viscosity of the gelent solution. The polymer solution may have a viscosity of from 0.01 to 5%, from 0.01 to 3%, from 0.01 to 2%, from 0.1 to 5%, from 0.1 to 3%, or from 0.1 to 2% of a viscosity of the gelent solution.

In embodiments, the polymer solution may include total dissolved solids of from 5,000 to 200,000 mg/L, from 10,000 to 200,000 mg/L, from 15,000 to 200,000 mg/L, from 20,000 to 200,000 mg/L, from 25,000 to 200,000 mg/L, from 30,000 to 200,000 mg/L, from 35,000 to 200,000 mg/L, from 5,000 to 120,000 mg/L, from 10,000 to 120,000 mg/L, from 15,000 to 120,000 mg/L, from 20,000 to 120,000 mg/L, from 25,000 to 120,000 mg/L, from 30,000 to 120,000 mg/L, from 35,000 to 120,000 mg/L, from 5,000 to 80,000 mg/L, from 10,000 to 80,000 mg/L, from 15,000 to 80,000 mg/L, from 20,000 to 80,000 mg/L, from 25,000 to 80,000 mg/L, from 30,000 to 80,000 mg/L, or from 35,000 to 80,000 mg/L.

The third core plug 130 may be saturated with a gelent solution. The gelent solution may include a polymer and a crosslinker. The gelent solution may include any of the polymers previously described in conjunction with the polymer solution. In embodiments, the polymer of the gelent solution may be the same as the polymer used in the polymer solution. The crosslinker may include at least one of hexamethylenetetramine, resorcinol, chromium acetate, chromium malonate, and polyethyleneimine. In some embodiments, the gelent solution may include at least one polymer, hexamethylenetetramine, and resorcinol.

The method may further include saturating the first core plug 110, the second plug 120, and the third core plug 130 with an aqueous solution. The aqueous solution may have a viscosity of less than 50 cP, less than 20 cP, less than 15 cP, less than 10 cP, less than 8 cP, less than 5 cP, or less than 2 cP. The method may further include saturating the third core plug 130 with the gelent solution by displacing the aqueous solution with the gelent solution. The method may further include saturating the first core plug 110 and the second core plug 120 with the polymer solution by displacing the aqueous solution with the polymer solution. Prior to saturating the first core plug 110 and the second core plug 120 with the polymer solution and the third core plug 130 with the gelent solution, the first core plug 110, the second plug, and third core plug 130 may be saturated with the aqueous solution.

The aqueous solution may include one or more than one of fresh water, salt water, brine, connate brine, municipal water, formation water, produced water, well water, filtered water, distilled water, sea water, or combinations of these. The aqueous solution may include water or a solution containing water and one or more inorganic compounds, such as but not limited to salts, dissolved in the water or otherwise completely miscible with the water. In embodiments, the aqueous solution may contain brine, including natural and synthetic brine. Brine may include water and a salt that may include calcium chloride, calcium bromide, sodium chloride, sodium bromide, other salts, and combinations of these. The aqueous solution may include total dissolved solids of from 0 to 300,000 mg/L.

Still referring to FIG. 1, as previously discussed in this disclosure, the methods further include alternating the polymer solution injections between a first injection area 112 located on the first core plug 110 and a second injection area 122 located on the second core plug 120. The first injection area 112 may be a portion of an outer axial surface 114 of the first core plug 110, where the outer axial surface 114 of the first core plug 110 is a surface of the first core plug 110 facing in an axial direction away from the third core plug 130 relative to the center axis A of the composite core plug 100. The second injection area 122 may be a portion of an outer axial surface 124 of the second core plug 120, where the outer axial surface 124 of the second core plug 120 is a surface of the second core plug 120 facing in an axial direction away from the third core plug 130 relative to the center axis A of the composite core plug 100. The polymer solution may be injected in an injection point or may be injected over the entire exposed face, or surface, of the first core plug 110 or the second core plug 120, such over the entire outer axial surface 114 of the first core plug 110 and the outer axial surface 124 of the second core plug 120, respectively.

Injecting the polymer solution may reduce or prevent viscous fingering and dispersion of the polymer solution into the gelent solution during subsequent injection compared to injection of a solution with a viscosity of less than 10 cP. This may be due to the similar viscosities of the polymer solution and the gelent solution. When the viscosity of a displacing fluid is lesser than that of displaced fluid, the displacing fluid will exhibit less resistance and a tendency to advance faster. This difference in viscosity can lead to viscous fingering, where instabilities arise in the form of the less viscous fluid displacing or fingering through the more viscous fluid. Therefore, if a solution with a viscosity less than 10 cP is injected, it will finger through the polymer solution and have a tendency of breaking into the gelent solution in the third core plug 130 and diluting the gelent solution, which will yield an inaccurate gel stability. It is not viable to inject the gelent solution because the gel would form at the injection areas, or outside the core plug, and block the inlet and outlet injection tubing of the coreholder. Using the polymer solution as the injection solution may prevent the gel from forming at the injection areas and yield a more uniform displacement, which may reduce or prevent viscous fingering and yield a more accurate gel stability.

The polymer solution may be injected into the composite core plug 100 where pressures are monitored to observe the gel stability with conventional coreholders, and without the need for pressure taps. The pressures may be monitored downstream of the injection areas, or upstream of the injection areas, or at a location proximate the injection areas.

Alternating the polymer solution injection area may ensure that the gelent solution remains within the third core plug 130 of the composite core plug 100, so that the measured gel stability is accurate for the gel in the porous media of the third core plug 130. By continuously injecting the polymer solution, the testing method may more accurately simulate in situ gelent solution injection conditions. When a gelent solution is injected downhole into a formation, the gelent solution is being continuously pumped into the formation, meaning that the gelent solution is in a state of constant flow. Once gelled in the formation, additional treatment fluids are pumped into the formation and are diverted by the gel. Thus, during gel formation and further during the lifespan of the gel installed in the formation, the gel is subjected to a dynamic flow environment, which exposes the gel to various fluids and forces within the formation. Therefore, continuously injecting the polymer solution into the composite core plug more accurately simulates in situ conditions of the gel in the subterranean hydrocarbon bearing formation, resulting in a more accurate measurement of gel stability.

In embodiments, each alternating polymer solution injection may include injecting from 0.01 to 1.0 times, from 0.01 to 0.5 times, from 0.01 to 0.4 times, from 0.01 to 0.3 times, from 0.01 to 0.2 times, from 0.1 to 1.0 times, from 0.1 to 0.5 times, from 0.1 to 0.4 times, from 0.1 to 0.3 times, or from 0.1 to 0.2 times of the total pore volume of the third core plug 130 per injection. Alternating injection of the polymer solution may include injecting a first volume of the polymer solution of from 0.01 to 1.0 times, from 0.05 to 1.0 times, from 0.08 to 1.0 times, from 0.1 to 1.0 times, from 0.15 to 1.0 times, from 0.2 to 1.0 times, from 0.01 to 0.8 times, from 0.05 to 0.8 times, from 0.08 to 0.8 times, from 0.1 to 0.8 times, from 0.15 to 0.8 times, from 0.2 to 0.8 times, from 0.01 to 0.5 times, from 0.05 to 0.5 times, from 0.08 to 0.5 times, from 0.1 to 0.5 times, from 0.15 to 0.5 times, or from 0.2 to 0.5 times the total pore volume of the second core plug 120 per injection into the first injection area 112. Alternating injection of the polymer solution may include injecting a second volume of the polymer solution of from 0.01 to 1.0 times, from 0.05 to 1.0 times, from 0.08 to 1.0 times, from 0.1 to 1.0 times, from 0.15 to 1.0 times, from 0.2 to 1.0 times, from 0.01 to 0.8 times, from 0.05 to 0.8 times, from 0.08 to 0.8 times, from 0.1 to 0.8 times, from 0.15 to 0.8 times, from 0.2 to 0.8 times, from 0.01 to 0.5 times, from 0.05 to 0.5 times, from 0.08 to 0.5 times, from 0.1 to 0.5 times, from 0.15 to 0.5 times, or from 0.2 to 0.5 times the total pore volume of the first core plug 110 per injection into the second injection area 122.

The volume of each alternating polymer solution injection, alternatively, may be determined from and limited by the pore volumes of the first core plug 110 and the second core plug 120 to reduce or prevent dilution of the gelent mixture. Specifically, to ensure the gelent solution in the third core plug 130 is not ejected from the composite core plug 100, the maximum permissible pore volume to be injected may be the pore volume of the opposing end plug. For instance, the pore volume injected into the first core plug 110 may be less than or equal to the total pore volume of the second core plug 120. Similarly, the pore volume injected into the second core plug 120 may be less than or equal to the total pore volume of the first core plug 110. In embodiments, the amount of polymer solution injected into the first core plug 110 may be less than or equal to 1.0 pore volume (PV) of the second core plug 120, less than or equal to 0.5 PV, less than or equal to 0.4 PV, less than or equal to 0.3 PV, less than or equal to 0.25 PV, less than or equal to 0.2 PV, less than or equal to 0.15 PV, or even less than or equal to 0.1 PV of the second core plug 120. In embodiments, the amount of polymer solution injected into the second core plug 120 may be less than or equal to 1.0 pore volume (PV) of the first core plug 110, less than or equal to 0.5 PV, less than or equal to 0.4 PV, less than or equal to 0.3 PV, less than or equal to 0.25 PV, less than or equal to 0.2 PV, less than or equal to 0.15 PV, or even less than or equal to 0.1 PV of the first core plug 110.

Alternating injection of the polymer solution may include injecting the polymer solution at a constant flow rate. Injecting the polymer solution at constant flow rate in alternating directions into a porous medium may provide mixing and agitation to the gelent solution. Agitating the gelent solution, which includes the polymer and crosslinker, may trigger crosslinking of the polymer chains, which causes the onset of gelation. Injecting the polymer solution at constant flow rate in alternating directions may keep the gel flowing back to the third core plug 130 after each injection. The continuous alternating flow of the methods of the present disclosure better replicates the in situ conditions of pumping the gelent solution into a formation by simulating constant flow, therefore more accurately measuring the gel long-term stability and generating more representative data.

In embodiments, the polymer solution may be alternatively injected at a constant flow rate of from 0.05 to 0.2 milliliter per minute (ml/min) (0.00083 to 0.0033 cubic centimeters per second (cc/s); 1 ml/min=0.0167 cc/s), from 0.05 to 0.15 ml/min (from 0.00083 cc/s to 0.0025 cc/s), from 0.05 to 0.1 ml/min (from 0.00083 cc/s to 0.00167 cc/s), from 0.08 to 0.2 milliliter per minute (ml/min) (0.0013 cc/s to 0.0033 cc/s), from 0.08 to 0.15 ml/min (from 0.0013 cc/s to 0.0025 cc/s), from 0.08 to 0.1 ml/min (from 0.0013 cc/s to 0.00167 cc/s), or 0.1 ml/min (0.00167 cc/s), into the first injection area 112, second injection area 122, or both.

To evaluate gel stability of a gel in situ at reservoir conditions, the alternating injection of the polymer solution into the first injection area 112 and the second injection area 122 may be conducted at in situ confining pressure and temperature. The confining pressure and temperature may vary depend on the depth, type of formation, and reservoir conditions meant to be simulated. The confining pressure may be from 200 to 3000 psi (from 1378.95 to 20684.27 kPa), from 200 to 2500 psi (from 1378.95 to 17236.89 kPa), from 200 to 2000 psi (from 1378.95 to 13789.51 kPa), from 300 to 3000 psi (from 2068.43 to 20684.27 kPa), from 300 to 2500 psi (from 2068.43 to 17236.89 kPa), from 300 to 2000 psi (from 2068.43 to 13789.51 kPa), from 500 to 3000 psi (from 3447.38 to 20684.27 kPa), from 500 to 2500 psi (from 3447.38 to 17236.89 kPa), or from 500 to 2000 psi (from 3447.38 to 13789.51 kPa). The temperature may be from 50 to 150° C., from 50 to 125° C., from 50 to 115° C., from 50 to 110° C., from 80 to 150° C., from 80 to 125° C., from 80 to 115° C., from 80 to 110° C., from 90 to 150° C., from 90 to 125° C., from 90 to 115° C., from 90 to 110° C., from 95 to 150° C., from 95 to 125° C., from 95 to 115° C., or from 95 to 110° C.

Still referring to FIG. 1, the alternating injections of the polymer solution into the first injection area 112 and the second injection area 122 may be conducted with a specific backpressure. The term "backpressure" may refer the pressure opposed to the desired flow of liquids registered on testing equipment. The backpressure may be the actual reservoir pressure. The backpressure may be from 25 to 4500 psi (from 172.36 to 31026.4 kPa), from 25 to 3500 psi (from 172.36 to 24131.7 kPa), from 25 to 3000 psi (from 172.36 to 20684.3 kPa), from 25 to 2500 psi (from 172.36 to 17236.9 kPa), from 50 to 4500 psi (from 344.738 to 31026.4 kPa), from 50 to 3500 psi (from 344.738 to 24131.7 kPa), from 50 to 3000 psi (from 344.738 to 20684.3 kPa), from 50 to 2500 psi (from 344.738 to 17236.9 kPa), from 80 to 4500 psi (from 551.58 to 31026.4 kPa), from 80 to 3500 psi (from 551.58 to 24131.7 kPa), from 80 to 3000 psi (from 551.58 to 20684.3 kPa), from 80 to 2500 psi (from 551.58 to 17236.9 kPa), from 100 to 4500 psi (from 689.476 to 31026.4 kPa), from 100 to 3500 psi (from 689.476 to 24131.7 kPa), from 100 to 3000 psi (from 689.476 to 20684.3 kPa), or from 100 to 2500 psi (from 689.476 to 17236.9 kPa).

The method may further include identifying a gelation of the gelent solution, where the gelation is indicated by an increase in the pressure drop across the composite core plug 100. The increase in the pressure drop across the composite core plug 100 indicative of gelation of the gelent solution to form a gel may be characterized by an increase in an average slope of the pressure drop across the composite core plug 100 as a function of a logarithm of the time. For any point in time, the average slope of the pressure drop across the composite core plug 100 as a function of the logarithm of the time may be taken as an average over a period of one hour centered on the point in time. Generally, the pressure increase is relatively slow at first, indicated as smaller pressure slope (pressure drop line 210 in FIG. 3). After some time, the pressure increase becomes more significant, which is indicated by the steeper pressure slope (pressure drop line 220 in FIG. 3). The crossover point 212 of these two pressure drop lines 210 and 220 represents the gelation time.

The pressure drop across the composite core plug 100 may continue to increase after the start of gelation until the gelent solution is fully converted into the gel in the third core plug 130. Completion of gelation of the gelent solution to form the gel may be characterized by a plateauing or leveling-off of the pressure drop across the composite core plug 100. The conclusion of the gelation period may be characterized by a decrease in the slope of the pressure drop as a function of the logarithm of the time. When the pressure drop across the composite core plug 100 stops increasing or levels off, gelation of the gelent solution to produce the gel in the third core plug 130 is considered to be complete, which is indicated by point 222 in FIG. 3.

Referring again to FIG. 3, the pressure drop across the composite core plug 100 as a function of the time, with time on a logarithmic scale is graphically depicted. In FIG. 3, line segment 210 represents the gradual increase in the pressure drop across the composite core plug 100 at the beginning of the gelation process. After some time, the pressure drop increase becomes more significant. The slope of the trend line 220 fit to the pressure drop versus logarithm of time data has a slope that is substantially greater than the slope of trend line 210 of the pressure drop versus logarithm of time data. The crossover point, 212 in FIG. 3, is defined as the gelation time. Gelation of the gelent solution to form the gel continues along trend line 220 until the gel is fully formed in the third core plug 130, at which point the pressure drop as a function of the logarithm of time levels off. In FIG. 3, the point at which the gel is considered to be fully formed is noted at point 222, which is considered the end of the gelation period. From point 222, the pressure drop across the composite core plug 130 may remain generally constant as long as the gel continues to remain stable in the third core plug 130.

Referring again to FIG. 1, the methods of the present disclosure may further include evaluating the gel stability of the gel formed in the third core plug 130. The gel stability of the gel may be evaluated by continuing the alternating injections of the polymer solution into the first injection area 112 and the second injection area 122 after the increase in the pressure drop indicative of a gelation point and monitoring the pressure drop for a reduction in pressure drop indicative of deterioration of the gel. Referring again to FIG. 3, during the continuation of the alternating injections, the pressure drop across the composite core plug 100 may remain generally constant between the completion of gelation and the start of deterioration of the gel, as indicated by the trend line 230.

The alternating injections of the polymer solution into the first injection area 112 and the second injection area 122 may be continued until the pressure drop across the composite core plug 100 as a function of time indicates the start of deterioration of the gel in the third core plug 130. The methods of the present disclosure may further include identifying a reduction in the pressure drop, a change in the slope of the pressure drop as a function of the logarithm of time, or both across the composite core plug indicative of deterioration of the gel. Referring again to FIG. 3, at point 304, the pressure drop across the composite core plug 100 begins to decrease and the slope of the pressure drop as a function of the logarithm of the time changes, which may indicate that the gel in the third core plug 130 is becoming unstable and beginning to break down. The reduction in the pressure drop indicative of deterioration of the gel may include at least a 10% reduction in the pressure drop across the composite core plug 100 over a period of less than or equal to 24 hours.

The reduction in the pressure drop across the composite core plug 100 indicative of deterioration of the gel may be characterized by a change in an average slope of the pressure drop as a function of a logarithm of the time. In particular, the reduction in the pressure drop across the composite core plug 100 indicative of deterioration of the gel may be identified by a decrease in the average slope of the pressure drop as a function of the logarithm of time. As shown in FIG. 3, at point 304, the slope of the pressure drop changes from a relatively flat slope along trendline 230 to a steeply negative slope along trendline 310. The change in slope of the pressure drop to a steep negative slope along trendline 310 indicates instability in the gel leading to disintegration of the gel in the third core plug 130. The point 304 where the pressure drop starts decreasing rapidly may be referred to as the start of syneresis. Syneresis may be characterized by expulsion of liquid from the gel, which may cause the gel to separate and break down. Syneresis of the gel tends to be more significant at first as indicated by the steeper slope (greater absolute value of the slope) of the pressure drop trendline 310 in FIG. 3. After some time, the gel syneresis slows down. The slope of the pressure drop as a function of the logarithm of time may increase again, such as becoming flatter (less steep or less negative), as shown by trendline 320 in FIG. 3. The gel disintegration process may continue for a long time. The permeability gradually restores (increases) during gel disintegration. However, despite the permeability gradually restoring, the gel may still provide some residual blocking effect in the composite core plug, indicating the gel composition may provide some continued blocking effect in a subterranean formation despite the gel disintegration.

The stability of a gel may be evaluated based on the time duration elapsed between formation of the gel at point 222 and the start of syneresis at point 304 in FIG. 3. The stability of the gel may be further characterized by a deterioration time, which may be the total amount of time it takes for the gel to deteriorate to a point where the gel deterioration becomes insignificant. The deterioration time may be the time that elapses between point 304 and point 312 in FIG. 3, or between point 304 to the time when the permeability through the composite core plug restores to greater than or equal to 80%, or even greater than or equal to 90% of the original value. The stability of the gel may be evaluated based on the total time duration elapsed between the formation gel at point 222 to point 312 or to the time when permeability restores to greater than or equal to 80% or even greater than or equal to 90% of the original value.

The stability of the gel may further be evaluated by evaluating the strength of the gel during the syneresis period. The strength of the gel may be related to the ability of the gel to continue to provide at least some barrier to fluid flow during disintegration of the gel. The strength of the gel during deterioration can be assessed by evaluating the rate of deterioration of the gel. The rate of deterioration of the gel may be determined by dividing the total decrease in pressure drop during syneresis (trendline 310 in FIG. 3) by the deterioration time. For a stable gel during deterioration, the rate of deterioration of the gel may be slower compared to a less stable gel. Thus, for a stable gel, the gel may provide a barrier to fluid flow for a longer period of time compared to a less stable gel. The gel stability of the gel may be evaluated based on the deterioration time, rate of deterioration of the gel, or both.

EXAMPLES

The following example illustrates features of the present disclosure but is not intended to limit the scope of the disclosure.

Comparative Example 1— Bottle Test

Figure 4:
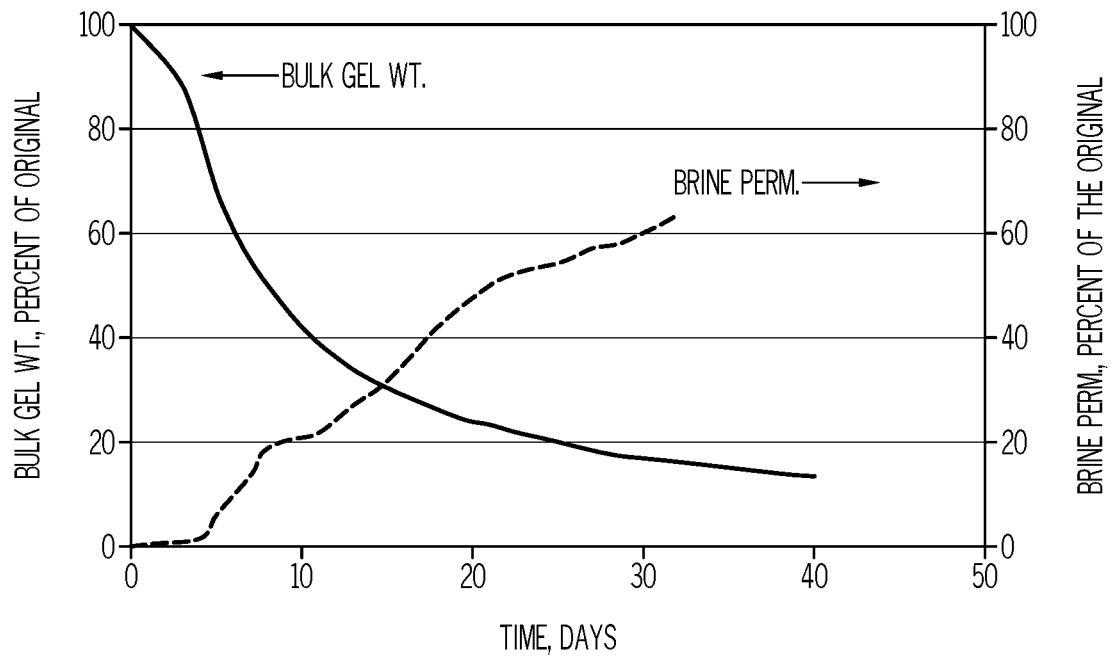
FIG. 4 graphically depicts bulk gel weight reduction and brine permeability restoration (y-axis) as a function of the logarithm of time (x-axis) after gel treatment, according to Comparative Example 1.

The stability of bulk gel was evaluated by measuring gel syneresis with time at high temperature. In this example, the gel weight reduction with time was measured. A bottle test was conducted at 95° C. with a 30 cubic centimeter (cm³) gel sample placed in a 40 cm³ bottle. The gel sample was composed of 5000 parts per million by weight (ppmw) polymer and 500 ppmw Cr(III). The gel sample is sealed in the glass bottle and put into an oven at 95° C. to form the gel. Once gel syneresis is observed, the gel sample is periodically taken out from the oven and the gel weight is measured. The sample is firstly left to cool down close to room temperature. Later, the water expelled from the gel structure is removed prior to weighting. Finally, the expelled water is put back into the glass bottle before returning the sample into the oven for further aging. The results from bottle tests were basically the shrinkage of gel observed in the bottle post gelation. In FIG. 4, the bulk gel weight reduction as a function of the time, with time on a logarithmic scale is graphically depicted. The bottle test results do not represent the actual behavior in the formation because the bottle test does not include the interactions between the gel and the rock.

Comparative Example 2— Conventional Core Flood Test

In Comparative Example 2, a conventional coreflooding test and conventional core plugs were used for evaluating gel stability. A core plug, with 4.28 cm in length and 3.81 cm in diameter, was used in this example. Its porosity was 25.1%, and permeability was 2985 md. A synthetic connate brine with total dissolved solids (TDS) of 213,730 mg/L was prepared for saturating core plug samples. A synthetic sea water with TDS of 57,670 mg/L was used to prepare polymer solutions. Detailed brine compositions are presented in Table 1. The same gel sample as used in Example 1 for bottle test was used for this example, which composed of 5000 ppmw polymer and 500 ppmw Cr(III). The polymer used for the test was a copolymer of acrylamide and arcylamide tert-butyl sulfonate with a sulfonation degree of about 25%. The molecular weight of the polymer was 12 million.

TABLE 1

Synthetic brine compositions.

| | $Na^+$, mg/L | $Ca^{2+}$, mg/L | $Mg^{2+}$, mg/L | $Cl^-$, mg/L | $HCO_3^-$, mg/L | $SO_4^{2-}$, mg/L | TDS, mg/L |
|---|---|---|---|---|---|---|---|
| Connate brine | 59,491 | 19,040 | 2,439 | 132,060 | 354 | 350 | 213,730 |
| Sea water | 18,300 | 650 | 2,110 | 32,200 | 120 | 4,290 | 57,670 |

The clean and dry core plug was first fully saturated with the synthetic connate brine under vacuum. The plug was then loaded into a coreholder, and its base permeability to brine was measured. Then, 1.0 pore volume (PV) of the gel solution was injected into the core sample, and then soaked for 24 hours at 95° C. The restoration of brine permeability was then periodically measured until the increase in brine permeability became insignificant, such as permeability restoring to greater than 80% or even greater than 90% of the original value. A confining pressure of 1400 psi and a backpressure of 200 psi were used in the test, and all the test was conducted at 95° C.

The results from coreflood testing were interpreted in terms of permeability restoration which is basically the disappearance of any created Residual Resistance Factor (RRF). RRF is the ratio of water (injecting fluid) mobility before gel injection to the water mobility after gel treatment. It is a measure of the water permeability reduction after the application of gel treatment. If the water is injected at a same flow rate before and after gel injection, then the residual resistance factor can be calculated as follows, $$RRF = \frac{\lambda_w}{\lambda'_w} = \frac{k_w}{k'_w} = \frac{\Delta P'_w}{\Delta P_w}$$

where $\lambda_w$, $k_w$ and $\Delta P_w$ are water mobility, water permeability and pressure drop before gel injection, respectively. $\lambda'_w$, $k'_w$ and $\Delta P'_w$ are water mobility, water permeability and pressure drop after gel injection, respectively.

Figure 5:
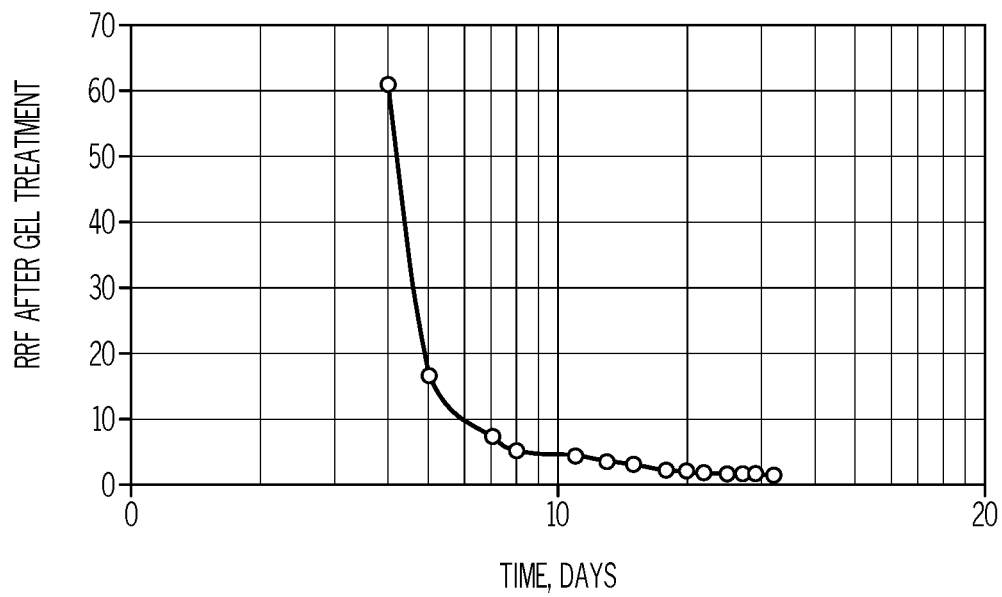
FIG. 5 graphically depicts a Residual resistance factor (RRF) (y-axis) as a function of the logarithm of time (x-axis) after gel treatment, according to Comparative Example 2.

The brine permeability restoration versus time after gel treatment is plotted in FIG. 4, for comparison with the bottle test result on the bulk gel. In FIG. 5, RRF as a function of the time, with time on a logarithmic scale is graphically depicted. The RRF decrease represents permeability restoration, an indication of the loss in gel stability. The coreflooding test results do not represent the actual behavior in the formation because RRF was measured periodically with periods between measurements where the gel was maintained in a static condition. In most of the time, the gel was in a static condition. A part of gel was flushed out of the core by injecting brine in one direction only.

Inventive Example 3

In Inventive Example 3, gel stability is evaluated using the composite core plug as depicted in FIG. 1. The test is conducted at 95° C., with 200 psi (1.38 MPa) pore pressure and 1400 psi (9.65 MPa) confining pressure being applied. FIG. 3 graphically depicts a differential pressure (y-axis) as a function of the logarithm of time (x-axis) during gelation time and gel stability testing, according to Inventive Example 3. Compared to Comparative Examples 1 and 2, Inventive Example 3 could evaluate gel long-term stability as well as gelation time accurately utilizing core plugs and coreholders.

A first aspect of the present disclosure may be directed to a method of evaluating gel stability of a gel for treating a subterranean formation may include placing a composite core plug into a core holder of a coreflood testing device. The composite core plug may comprise a first core plug, a second core plug, and a third core plug disposed between the first core plug and the second core plug. The first core plug and second core plug may be saturated with a polymer solution. The third core plug may be saturated with a gelent solution comprising at least a polymer and a crosslinker. The method may further include alternating injection of the polymer solution into a first injection area located on the first core plug and a second injection area located on the second core plug, monitoring a pressure drop across the composite core plug as a function of time, identifying a gelation of the gelent solution. The gelation may be indicated by an increase in the pressure drop across the composite core plug. The method may further include after the increase in the pressure drop indicative of a gelation point, continuing alternating injections of the polymer solution into the first injection area and the second injection area, and, identifying a reduction in the pressure drop across the composite core plug indicative of deterioration of the gel. The reduction in the pressure drop indicative of deterioration of the gel may comprise at least a 10 percent (%) reduction in the pressure drop across the composite core plug over a period of less than or equal to 24 hours. The gel stability may be indicated by a time elapsed between the increase in the pressure drop indicative of gelation and the reduction in the pressure drop indicative of deterioration of the gel.

A second aspect of the present disclosure may include the first aspect, where the increase in the pressure drop across the composite core plug indicative of gelation of the gelent solution to form a gel may be characterized by a step increase in an average slope of the pressure drop as a function of a logarithm of the time; and the average slope is taken over a period of 1 hour.

A third aspect of the present disclosure may include either one of the first or second aspects, where the reduction in the pressure drop across the composite core plug indicative of deterioration of the gel may be characterized by a step decrease in an average slope of the pressure drop as a function of a logarithm of the time; and the average slope takes over a period of 1 hour. In embodiments, the reduction in the pressure drop across the composite core plug indicative of deterioration of the gel may be characterized by an increase in the magnitude of the absolute value of the average slope of the pressure drop as a function of a logarithm of the time; and the average slope takes over a period of 1 hour.

A fourth aspect of the present disclosure may include any one of the first through third aspects, further comprising, after an initial reduction in the pressure drop indicative of initiation of disintegration of the gel, continuing alternating injections of the polymer solution into the first injection area and the second injection area; and identifying a disintegration time equal to a time elapsed between the initial reduction in the pressure drop indicative of initiation of disintegration of the gel and insignificant reduction in the pressure drop indicate of completion of disintegration of the gel.

A fifth aspect of the present disclosure may include any one of the first through fourth aspects, wherein the permeability through the composite core plug restores to greater than or equal to 80%, or even greater than or equal to 90% of the original value.

A sixth aspect of the present disclosure may include any one of the first through fifth aspects, further comprising calculating a total rate of disintegration of the gel from a total change in the pressure drop and the disintegration time.

A seventh aspect of the present disclosure may include any one of the first through sixth aspects, comprising continuing alternating injections of the polymer solution into the first injection area and the second injection area after gelation of the gelent solution to produce the gel is complete and until the permeability restoration becomes insignificant.

An eighth aspect of the present disclosure may include any one of the first through seventh aspects, where alternating injection of the polymer solution into the first injection area and the second injection area may further comprise injecting from 0.01 to 1.0 times the total pore volume of the third core plug per alternating injection.

A ninth aspect of the present disclosure may include any one of the first through eighth aspects, where alternating injection of the polymer solution may further comprise injecting a first volume of the polymer solution of from 0.01 to 1.0 times the total pore volume of the second core plug per injection into the first injection area; and injecting a second volume of the polymer solution of from 0.01 to 1.0 times the total pore volume of the first core plug per injection into the second injection area.

An tenth aspect of the present disclosure may include any one of the first through ninth aspects, where alternating injection of the polymer solution may further comprise injecting equal amounts of the polymer solution in each alternating injection.

An eleventh aspect of the present disclosure may include any one of the first through tenth aspects, where alternating injection of the polymer solution may further comprise injecting the polymer solution at a constant flow rate.

A twelfth aspect of the present disclosure may include any one of the first through eleventh aspects, where the constant flow rate may be from 0.01 milliliters per minute (ml/min) to 10 ml/min.

A thirteenth aspect of the present disclosure may include any one of the first through twelfth aspects, where the polymer solution does not include crosslinker.

A fourteenth aspect of the present disclosure may include any one of the first through thirteenth aspects, comprising alternating injection of the polymer solution into the first injection area and the second injection area at a net confining pressure of from 200 pounds per square inch (psi) (1378.95 kPa) to 3000 psi (20684.27 kPa).

A fifteenth aspect of the present disclosure may include any one of the first through fourteenth aspects, comprising alternating injection of the polymer solution into the first injection area and the second injection area with a backpressure of from 25 psi (172.36 kPa) to 4500 psi (31026.4 kPa).

A sixteenth aspect of the present disclosure may include any one of the first through fifteenth aspects, comprising alternating injection of the polymer solution into the first injection area and the second injection area at a temperature of from 50 degrees Celsius (° C.) to 150° C.

A seventeenth aspect of the present disclosure may include any one of the first through sixteenth aspects, further comprising saturating the first core plug and second core plug with an aqueous solution.

An eighteenth aspect of the present disclosure may include any one of the first through seventeenth aspects, further comprising saturating the third core plug with the gelent solution and displacing the aqueous solution.

A nineteenth aspect of the present disclosure may include the eighteenth aspect, further comprising saturating the first core plug and the second core plug with the polymer solution and displacing the aqueous solution.

A twentieth aspect of the present disclosure may include any one of the first through nineteenth aspects, where the first core plug may comprise a diameter, porosity, and permeability within 0.1% of a diameter, porosity, and permeability of the second core plug.

A twenty-first aspect of the present disclosure may include any one of the first through twentieth aspects, where the polymer solution may comprise at least one of polyacrylamide, acrylamide copolymers, biopolymers, polysaccharides, and xanthan gum.

A twenty-second aspect of the present disclosure may include any one of the first through twenty-first aspects, where the crosslinker may comprise at least one of hexamethylenetetramine, resorcinol, chromium acetate, chromium malonate, and polyethyleneimine.

A twenty-third aspect of the present disclosure may include any one of the first through twenty-second aspects, where the polymer solution may have a viscosity within 5% of a viscosity of the gelent solution.

A twenty-fourth aspect of the present disclosure may include any one of the first through twenty-third aspects, where the polymer of the polymer solution may have a weight averaged molecular weight of from 10 million Daltons to 30 million Daltons.

It is noted that one or more of the following claims utilize the term "where" or "in which" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising." For the purposes of defining the present technology, the transitional phrase "consisting of" may be introduced in the claims as a closed preamble term limiting the scope of the claims to the recited components or steps and any naturally occurring impurities. For the purposes of defining the present technology, the transitional phrase "consisting essentially of" may be introduced in the claims to limit the scope of one or more claims to the recited elements, components, materials, or method steps as well as any non-recited elements, components, materials, or method steps that do not materially affect the novel characteristics of the claimed subject matter. The transitional phrases "consisting of" and "consisting essentially of" may be interpreted to be subsets of the open-ended transitional phrases, such as "comprising" and "including," such that any use of an open ended phrase to introduce a recitation of a series of elements, components, materials, or steps should be interpreted to also disclose recitation of the series of elements, components, materials, or steps using the closed terms "consisting of" and "consisting essentially of."

As used in the Specification and appended Claims, the singular forms "a", "an", and "the" include plural references unless the context clearly indicates otherwise. The verb "comprises" and its conjugated forms should be interpreted as referring to elements, components or steps in a non-exclusive manner. The referenced elements, components or steps may be present, utilized or combined with other elements, components or steps not expressly referenced.

It should be understood that any two quantitative values assigned to a property may constitute a range of that property, and all combinations of ranges formed from all stated quantitative values of a given property are contemplated in this disclosure. The subject matter of the present disclosure has been described in detail and by reference to specific embodiments. It should be understood that any detailed description of a component or feature of an embodiment does not necessarily imply that the component or feature is essential to the particular embodiment or to any other embodiment. Further, it should be apparent to those skilled in the art that various modifications and variations can be made to the described embodiments without departing from the spirit and scope of the claimed subject matter.

What is claimed is:

1. A method of evaluating gel stability of a gel for treating a subterranean formation, the method comprising:
   placing a composite core plug into a core holder of a coreflood testing device, where:
      the composite core plug comprises a first core plug, a second core plug, and a third core plug disposed between the first core plug and the second core plug;
      the first core plug and second core plug are saturated with a polymer solution; and
      the third core plug is saturated with a gelent solution comprising at least a polymer and a crosslinker;
   alternating injection of the polymer solution into a first injection area located on the first core plug and a second injection area located on the second core plug;
   monitoring a pressure drop across the composite core plug as a function of time;
   identifying a gelation of the gelent solution, where the gelation is indicated by an increase in the pressure drop across the composite core plug;
   after the increase in the pressure drop indicative of a gelation point, continuing alternating injections of the polymer solution into the first injection area and the second injection area; and
   identifying a reduction in the pressure drop across the composite core plug indicative of deterioration of the gel, where:
      the reduction in the pressure drop indicative of deterioration of the gel comprises at least a 10 percent (%) reduction in the pressure drop across the composite core plug over a period of less than or equal to 24 hours; and
      the gel stability is indicated by a time elapsed between the increase in the pressure drop indicative of gelation and the reduction in the pressure drop indicative of deterioration of the gel.

2. The method of claim 1, where:
   the increase in the pressure drop across the composite core plug indicative of gelation of the gelent solution to form a gel is characterized by a step increase in an average slope of the pressure drop as a function of a logarithm of the time; and
   the average slope is taken as an average over a period of 1 hour.

3. The method of claim 1, where:
   the reduction in the pressure drop across the composite core plug indicative of deterioration of the gel is characterized by a step increase in an average slope of the pressure drop as a function of a logarithm of the time; and
   the average slope is taken as an average over a period of 1 hour.

4. The method of claim 1, further comprising:
   after an initial reduction in the pressure drop indicative of initiation of disintegration of the gel, continuing alternating injections of the polymer solution into the first injection area and the second injection area; and
   identifying a disintegration time equal to a time elapsed between the initial reduction in the pressure drop indicative of initiation of disintegration of the gel and insignificant reduction in the pressure drop indicate of completion of disintegration of the gel.

5. The method of claim 1, comprising continuing alternating injections of the polymer solution into the first injection area and the second injection area after gelation of the gelent solution to produce the gel is complete, and until the permeability restoration becomes insignificant.

6. The method of claim 1, where alternating injection of the polymer solution further comprises:
injecting a first volume of the polymer solution of from 0.01 to 1.0 times the total pore volume of the second core plug per injection into the first injection area; and
injecting a second volume of the polymer solution of from 0.01 to 1.0 times the total pore volume of the first core plug per injection into the second injection area.

7. The method of claim 1, where alternating injection of the polymer solution further comprises injecting equal amounts of the polymer solution in each alternating injection.

8. The method of claim 1, where alternating injection of the polymer solution further comprises injecting the polymer solution at a constant flow rate.

9. The method of claim 8, where the constant flow rate is from 0.01 milliliters per minute (ml/min) to 10 ml/min.

10. The method of claim 1, where the polymer solution does not include crosslinker.

11. The method of claim 1, comprising alternating injection of the polymer solution into the first injection area and the second injection area at a net confining pressure of from 200 pounds per square inch (psi) (1378.95 kPa) to 3000 psi (20684.27 kPa).

12. The method of claim 1, comprising alternating injection of the polymer solution into the first injection area and the second injection area with a backpressure of from 25 psi (172.36 kPa) to 4500 psi (31026.4 kPa).

13. The method of claim 1, comprising alternating injection of the polymer solution into the first injection area and the second injection area at a temperature of from 50 degrees Celsius (° C.) to 150° C.

14. The method of claim 1, further comprising saturating the first core plug and second core plug with an aqueous solution.

15. The method of claim 14, further comprising saturating the third core plug with the gelent solution and displacing the aqueous solution.

16. The method of claim 14, further comprising saturating the first core plug and the second core plug with the polymer solution and displacing the aqueous solution.

17. The method of claim 1, where the first core plug comprises a diameter, porosity, and permeability within 0.1% of a diameter, porosity, and permeability of the second core plug.

18. The method of claim 1, where the polymer solution comprises at least one of polyacrylamide, acrylamide copolymers, biopolymers, polysaccharides, and xanthan gum.

19. The method of claim 1, where the crosslinker comprises at least one of hexamethylenetetramine, resorcinol, chromium acetate, chromium malonate, and polyethyleneimine.

20. The method of claim 1, where the polymer solution has a viscosity within 5% of a viscosity of the gelent solution.

* * * * *